United States Patent [19]

Toukan

[11] Patent Number: 4,806,173

[45] Date of Patent: Feb. 21, 1989

[54] METHOD OF CLEANING DENTAL APPLIANCES ARTIFICIAL DENTURES

[76] Inventor: Sameeh S. Toukan, 856 E. Phillip Dr., Phoenixville, Pa. 19460

[21] Appl. No.: 735

[22] Filed: Jan. 5, 1987

[51] Int. Cl.$^4$ .............................. B08B 3/08; C11D 7/28
[52] U.S. Cl. .................................. 134/42; 252/142; 252/174.19; 252/DIG.14; 252/173
[58] Field of Search .................... 252/100, 142, 174.19, 252/DIG.14, 173; 134/42

[56] References Cited

U.S. PATENT DOCUMENTS

| | | | |
|---|---|---|---|
| 2,201,098 | 5/1940 | McKim | 252/143 |
| 3,607,759 | 9/1971 | Barth | 252/100 |
| 3,652,420 | 3/1972 | Hill | 252/101 |
| 4,162,172 | 7/1979 | Longo | 134/1 |
| 4,180,467 | 12/1979 | Barth | 252/99 |
| 4,181,621 | 1/1980 | Raaf et al. | 252/99 |
| 4,459,217 | 7/1984 | Bogie | 252/174.14 |

FOREIGN PATENT DOCUMENTS 8101969  7/1981  PCT Int'l Appl. .

*Primary Examiner*—Prince E. Willis

[57] ABSTRACT

A simple, effective and inexpensive method for cleansing dental appliances comprises the immersion of the artificial denture in a dilute aqueous solution of a carboxylic acid having the structure R(Z)COOH, where "R" is a hydrocarbon chain and "Z" is a hydroxy, a halo or aryl radical.

5 Claims, No Drawings

METHOD OF CLEANING DENTAL APPLIANCES ARTIFICIAL DENTURES

BACKGROUND OF THE INVENTION

This invention relates to cleansing compositions and their methods of application. In particular, it relates to a method for cleansing dental appliances, such as artificial dentures. The cleansing composition consists essentially of dilute aqueous solution of one carboxylic acid, such as acetic, succinic, maleic, citric, mandalic and lactic acids. In general, these acids have the structure R(Z)COOH or its anhydride, where "R" is a hydrocarbon chain and "Z" is a radical comprising a halogen, a hydroxy, a carboxy or aryl radical.

According to the present invention, I found out surprisingly that after soaking the dental appliance in a simple aqueous acidic solution overnight, and washing with warm water the next morning, the said dental appliance is clean, free from any oral deposits. In some cases, the use of a brush when washing with water enhances the cleansing effect. What is really surprising is that the dental appliance could not be cleaned when some of the commercial cleansing products such as "Polident" are used. What is more surprising is the fact that after several months of weekly treatment, the dental appliance remains free of deposits for long periods and the cleansing period is required only every half month or even at longer intervals.

An applausable explanation is that the acid bonds to the surface and forms a thin invisible film on the surface of the dental appliance, thus protecting it from the tartar deposits.

PRIOR ART

Dental cleaning compositions that have been in use are composed of several ingredients. Some of those that contain acids have in addition, a base such as sodium bicarbonate. They are used in the form of a gel, paste, tablet, or powder. Both U.S. Pat. Nos. 3,652,420 & 3,839,213 provide compositions in gel form. U.S. Pat. No. 3,839,213 recommends a preferred combination of an acid component, a solvent component and a gelling component as well as an abrasive component (column 1, lines 50-54). U.S. Pat. No. 4,406,708 (column 2, lines 64-68 and column 3, lines 5-14 & 45-50) teaches that basically these cleansing compositions consist of a combination of 2 or more chemical substances in powder or tablet form which when dissolved in water, vigorously react with each other, producing gas bubbles. It is this effervescing solution which is thus intended to automatically remove the coating of tacky retention agent.

The main disadvantage of these formulations is that the cleansing agent becomes very expensive to the users. Moreover, when sodium bicarbonate is used as a component of the retention agent for the dental prosthesis, some of it is unavoidably dissolved in the saliva in the oral cavity, which results in neutralization of the natural acid in the stomach and disturbs the normal pH level of the gastric juice. Yet a third isadvantage is the complexity of utilizing such cleansing compositions.

SUMMARY OF THE INVENTION

It is an object of this invention to provide a very simple and inexpensive cleansing composition for dental appliances. Another object is to provide a simple process for cleaning dental prosthesis which utilizes a highly efficient and effective composition to remove tartar and other oral deposits which are normally very hard to remove completely. Yet, another object is to conduct the cleansing process using non-toxic compositions.

An approximately 5% aqueous solution of a carboxylic acid is prepared. Examples of such acids are: acetic, maleic, fumaric, succinic, citric or derivatives thereof such as the anhydrides, hydroxy acids, halogenated acids and aralkyl acids. The dental appliance is soaked in the aqueous solution overnight. The next morning, the dental appliance is washed with water. Using warm water or a brush will enhance the cleansing effect.

The acids of the invention are carboxylic acids of 1-6 carbons, containing one to five carboxylic groups which can be saturated or unsaturated, such as succinic and maleic acids. Derivatives of such acids can also be used, such as the anhydrides which when dissolved in water, hydrolyses back to the acid; the halo-substituted acids such as chloroacetic acid; the hydroxy acids, such as citric acid; and the aralkyl acids, such as mandelic acid.

Depending on the amount of the tartar deposits, a 3-10% concentration of the acid in water is recommended. However, a 4-6% concentration is normally and preferably used to give the required cleaning effect.

EXAMPLE 1

A dental appliance which is extensively covered with tartar and other oral deposits is soaked in 5-6% acetic acid (vinegar) overnight. The next day, it is washed with warm water. The dental appliance becomes clean & ready to use again.

EXAMPLE 2

The same results are obtained when maleic anhydride is substituted for acetic acid.

EXAMPLE 3

The same results are obtained when monochloroacetic acid is substituted for acetic acid.

EXAMPLE 4

Similar results are obtained when succinic acid is substituted for acetic acid.

EXAMPLE 5

The same results are obtained when fumaric acid is substituted for acetic acid.

EXAMPLE 6

The same results are obtained when mandelic acid is substituted for acetic acid.

EXAMPLE 7

Again, the same results are obtained when citric acid is substituted for acetic acid.

Similar cleansing effect can be obtained using lactic, $CH_3CH(OH)COOH$, tartaric $HOOC-CH(OH)CH(OH)-COH$ and gluconic acid $HO-CH_2-(CHOH)_4-COOH$.

What is claimed is:

1. A method of removing tartar and other oral deposits from artificial dentures which comprises soaking the dentures overnight in an aqueous solution of a carboxylic acid selected from the group consisting of mandelic acid, lactic acid and chlorinated acetic acid, then rinsing them with water.

2. The method of claim 1, wherein the concentration of the acid in the aqueous solution is 3% to 10%.

3. The method according to claim 1 where the mandelic acid is in the anhydride form.

4. The method according to claim 1, where the chlorinated acetic acid is momochloroacetic acid.

5. The method according to claim 1, where the chlorinated acetic acid is in the anhydride form.

* * * * *